United States Patent
Nguyen et al.

(10) Patent No.: US 11,517,427 B2
(45) Date of Patent: *Dec. 6, 2022

(54) SYSTEMS FOR ASSESSING AND CUTTING BIOPROSTHETIC TISSUE

(71) Applicant: Edwards Lifesciences Corporation, Irvine, CA (US)

(72) Inventors: Oanh H. Nguyen, Coto de Caza, CA (US); Ivan Jankovic, Roseville, MN (US); Diana Nguyen-Thien-Nhon, Irvine, CA (US); Juan C. Velez, Ladera Ranch, CA (US); Jon Boomgarden, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/390,130

(22) Filed: Jul. 30, 2021

(65) Prior Publication Data

US 2021/0353410 A1 Nov. 18, 2021

Related U.S. Application Data

(60) Division of application No. 16/459,543, filed on Jul. 1, 2019, now Pat. No. 11,076,953, which is a
(Continued)

(51) Int. Cl.
*A61F 2/24* (2006.01)

(52) U.S. Cl.
CPC .............. *A61F 2/2415* (2013.01); *A61F 2/24* (2013.01); *A61F 2/2472* (2013.01); *A61F 2240/001* (2013.01); *Y10T 83/0405* (2015.04)

(58) Field of Classification Search
CPC ........ A61F 2/2415; A61F 2/24; A61F 2/2472; A61F 2240/001; Y10T 83/0405
See application file for complete search history.

(56) References Cited

U.S. PATENT DOCUMENTS

| 365,873 A | 7/1887 | Spence et al. |
| 1,012,372 A | 12/1911 | Landenberger |

(Continued)

FOREIGN PATENT DOCUMENTS

| EP | 0133420 A2 | 2/1985 |
| WO | 9511047 A1 | 4/1995 |

(Continued)

OTHER PUBLICATIONS

"The Carpentier-Edwards Perimount Pericardial Bioprosthesis—Time is the Most Important Text," Baxter, No date..
(Continued)

*Primary Examiner* — Jonathan G Riley
(74) *Attorney, Agent, or Firm* — Guy Cumberbatch

(57) ABSTRACT

Systems, dies, and methods are provided for processing pericardial tissue. The method includes positioning a die-cut assembly over the pericardial tissue, the die-cut assembly including a die having a plate, a die pattern, and an opening, the die pattern attached to the plate, the opening formed in the plate to provide access to the pericardial tissue, and measuring a thickness of the tissue through the opening. The die-cut assembly may be mounted for automated vertical movement, and a platen on which the tissue is placed is capable of automated horizontal movement. Different target areas on the tissue can be assessed by measuring the thickness through the die, and when an area is deemed suitable the die pattern cuts a shape therefrom. The system is useful for cutting uniform thickness heart valve leaflets, and can be automated to speed up the process.

21 Claims, 7 Drawing Sheets

Related U.S. Application Data continuation of application No. 15/173,435, filed on Jun. 3, 2016, now Pat. No. 10,335,271, which is a division of application No. 13/538,684, filed on Jun. 29, 2012, now Pat. No. 9,358,107.

(60) Provisional application No. 61/503,471, filed on Jun. 30, 2011.

(56) References Cited

U.S. PATENT DOCUMENTS

| | | | |
|---|---|---|---|
| 1,688,308 A | 10/1928 | Harding | |
| 2,122,945 A | 7/1938 | Kleinschmidt | |
| 2,393,580 A | 1/1946 | Weiskopf | |
| 2,856,582 A | 10/1958 | Anderson | |
| 3,002,895 A | 10/1961 | Freedman | |
| 3,093,439 A | 6/1963 | Bothwell | |
| 3,110,112 A | 11/1963 | Dalgleish | |
| 3,532,016 A * | 10/1970 | Zeph | A61F 2/2415 83/462 |
| 3,870,789 A | 3/1975 | Mikat | |
| 3,927,422 A | 12/1975 | Sawyer | |
| 3,961,097 A | 6/1976 | Gravlee, Jr. | |
| 3,966,401 A | 6/1976 | Hancock et al. | |
| 4,050,893 A | 9/1977 | Hancock et al. | |
| 4,060,734 A | 11/1977 | Tilley et al. | |
| 4,082,507 A | 4/1978 | Sawyer | |
| 4,120,649 A | 10/1978 | Schechter | |
| 4,199,255 A | 4/1980 | Wilson et al. | |
| 4,213,319 A * | 7/1980 | Gold | B21D 28/06 33/783 |
| 4,323,358 A | 4/1982 | Lentz et al. | |
| 4,350,492 A | 9/1982 | Wright et al. | |
| 4,360,887 A | 11/1982 | Wilson et al. | |
| 4,388,735 A | 6/1983 | Ionescu et al. | |
| 4,405,327 A | 9/1983 | Pollock | |
| 4,624,822 A | 11/1986 | Arru et al. | |
| 4,648,881 A | 3/1987 | Carpentier et al. | |
| 4,687,483 A | 8/1987 | Fisher et al. | |
| 4,687,783 A | 8/1987 | Horrmann | |
| 4,725,961 A | 2/1988 | Pearl | |
| 4,770,665 A | 9/1988 | Nashef | |
| 4,786,287 A | 11/1988 | Nashef et al. | |
| 4,800,603 A | 1/1989 | Jaffe | |
| 4,876,758 A | 10/1989 | Rolloff et al. | |
| 4,911,713 A | 3/1990 | Sauvage et al. | |
| 4,972,351 A | 11/1990 | Reger et al. | |
| 4,990,131 A | 2/1991 | Dardik et al. | |
| 5,002,566 A | 3/1991 | Carpentier et al. | |
| 5,037,434 A | 8/1991 | Lane | |
| 5,068,086 A | 11/1991 | Sklenak et al. | |
| 5,089,971 A | 2/1992 | Gerber | |
| 5,104,405 A | 4/1992 | Nimni | |
| 5,116,564 A | 5/1992 | Jansen et al. | |
| 5,131,908 A | 7/1992 | Dardik et al. | |
| 5,163,955 A * | 11/1992 | Love | A61F 2/2496 623/901 |
| 5,275,954 A | 1/1994 | Wolfinbarger et al. | |
| 5,279,612 A | 1/1994 | Eberhardt | |
| 5,319,951 A * | 6/1994 | Da Re | B21D 28/005 72/347 |
| 5,376,110 A | 12/1994 | Tu et al. | |
| 5,425,741 A * | 6/1995 | Lemp | A61B 17/32 606/167 |
| 5,447,536 A | 9/1995 | Girardot et al. | |
| 5,500,015 A * | 3/1996 | Deac | A61F 2/2412 623/901 |
| 5,546,323 A | 8/1996 | Bacus et al. | |
| 5,549,666 A | 8/1996 | Hata et al. | |
| 5,595,571 A | 1/1997 | Jaffe et al. | |
| 5,613,982 A | 3/1997 | Goldstein | |
| 5,632,778 A | 5/1997 | Goldstein | |
| 5,640,779 A | 6/1997 | Rolloff et al. | |
| 5,662,705 A | 9/1997 | Love et al. | |
| 5,718,012 A | 2/1998 | Cavallaro | |
| 5,773,285 A | 6/1998 | Park | |
| 5,792,603 A | 8/1998 | Dunkelman et al. | |
| 5,882,918 A | 3/1999 | Goffe | |
| 5,899,937 A | 5/1999 | Goldstein et al. | |
| 5,902,937 A | 5/1999 | Amrani et al. | |
| 5,961,549 A * | 10/1999 | Nguyen | A61F 2/2472 623/2.12 |
| 5,984,936 A | 11/1999 | Mangubat et al. | |
| 6,160,264 A | 12/2000 | Rebiere | |
| 6,210,957 B1 | 4/2001 | Carpentier et al. | |
| 6,245,105 B1 | 6/2001 | Nguyen et al. | |
| 6,287,338 B1 | 9/2001 | Samowski et al. | |
| 6,334,873 B1 | 1/2002 | Lane et al. | |
| 6,371,983 B1 | 4/2002 | Lane | |
| 6,378,221 B1 | 4/2002 | Ekholm, Jr. et al. | |
| 6,413,275 B1 | 7/2002 | Nguyen et al. | |
| 6,497,713 B1 * | 12/2002 | Tompkins | A61F 2/2415 606/167 |
| 6,553,681 B2 | 4/2003 | Ekholm, Jr. et al. | |
| 6,567,761 B1 * | 5/2003 | Modesto | H01L 21/67271 702/82 |
| 6,837,902 B2 | 1/2005 | Nguyen et al. | |
| 7,208,000 B2 * | 4/2007 | Love | A61F 2/2415 30/360 |
| RE42,818 E * | 10/2011 | Cali | B23K 26/324 156/251 |
| 2001/0044656 A1 | 11/2001 | Williamson et al. | |
| 2002/0005073 A1 * | 1/2002 | Tompkins | A61F 2/2472 73/835 |
| 2002/0091441 A1 * | 7/2002 | Guzik | A61F 2/2415 623/901 |
| 2003/0028247 A1 | 2/2003 | Cali | |
| 2004/0024452 A1 * | 2/2004 | Kruse | A61F 2/2415 623/2.12 |
| 2006/0276888 A1 * | 12/2006 | Lee | A61F 2/2412 623/2.14 |
| 2007/0095698 A1 * | 5/2007 | Cambron | B65B 7/2878 53/485 |
| 2009/0299372 A1 | 12/2009 | Steiner et al. | |
| 2013/0012767 A1 * | 1/2013 | Nguyen | A61F 2/2472 600/36 |

FOREIGN PATENT DOCUMENTS

| | | |
|---|---|---|
| WO | 9522361 A1 | 8/1995 |
| WO | 9534332 A1 | 12/1995 |
| WO | 9604028 A1 | 2/1996 |
| WO | 9613227 A1 | 5/1996 |
| WO | 9721069 A1 | 6/1997 |
| WO | 0133420 A1 | 5/2001 |

OTHER PUBLICATIONS

Allied Fischer Scientific Product Catalogue, pp. 914, 1986.*.
Corresponding International Search Report No. PCT/US2012/045224, dated Nov. 7, 2012.
Sacks, "Biaxial Mechanical Behavior of Fixed Bovine Pericardium," Fifth World Biomaterials Congress, Toronto, Canada, May 29-Jun. 2, 1996..
Simionescu, et al., "Mapping of Glutaraldehyde-Treated Bovine Pericardium and Tissue Selection for Bioprosthetic Heart Valves," Journal of Biomedical Materials Research, vol. 27, 697-703, 1993..
Zioupos, et al., "Anistropic Elasticity and Strength of Glutaraldehyde Fixed Bovine Pericadium for Use in Pericardial Bioprosthetic Valves", Journal of Biomedical Materials Research, vol. 28, 49-57, 1994..

* cited by examiner

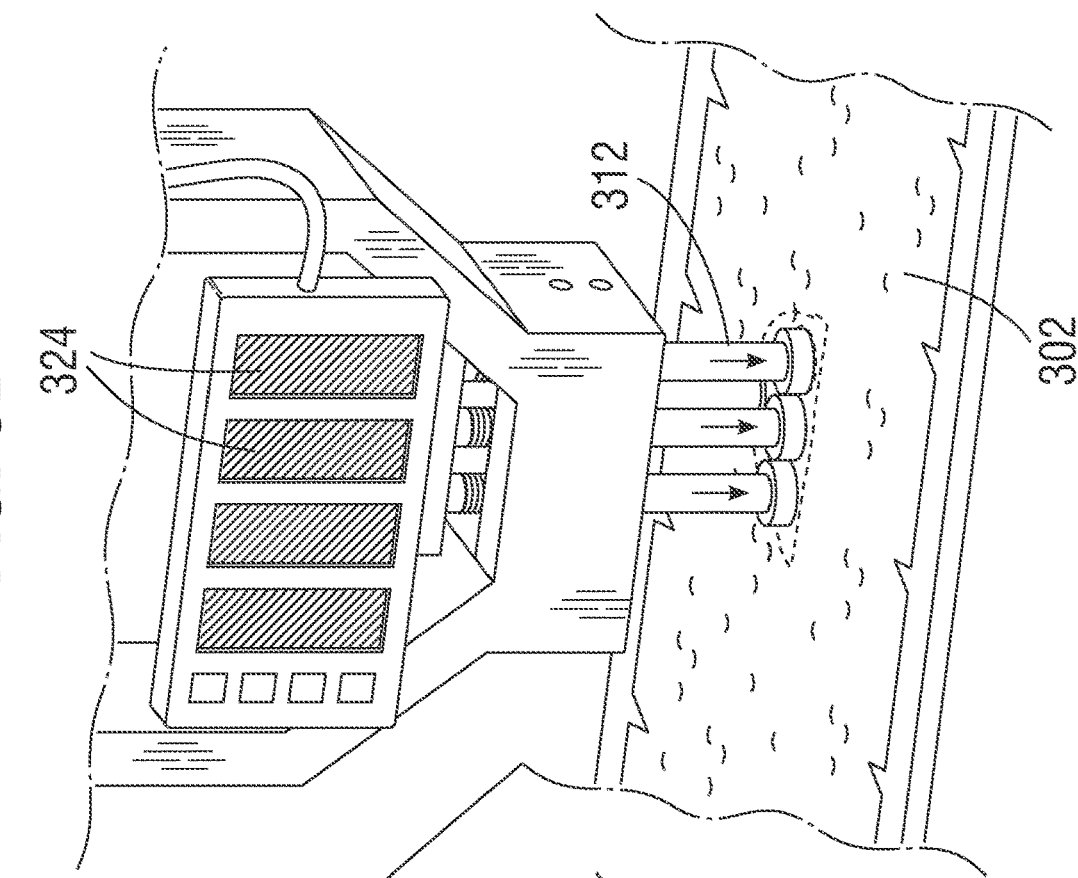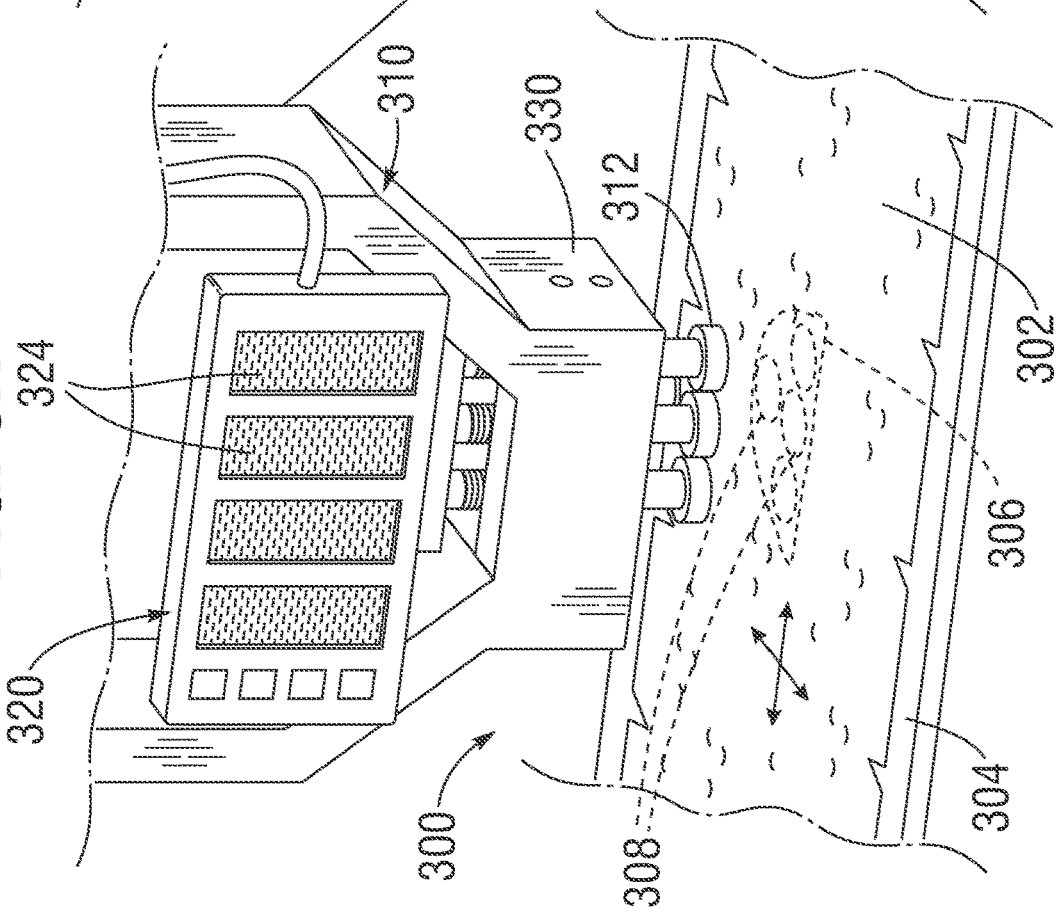

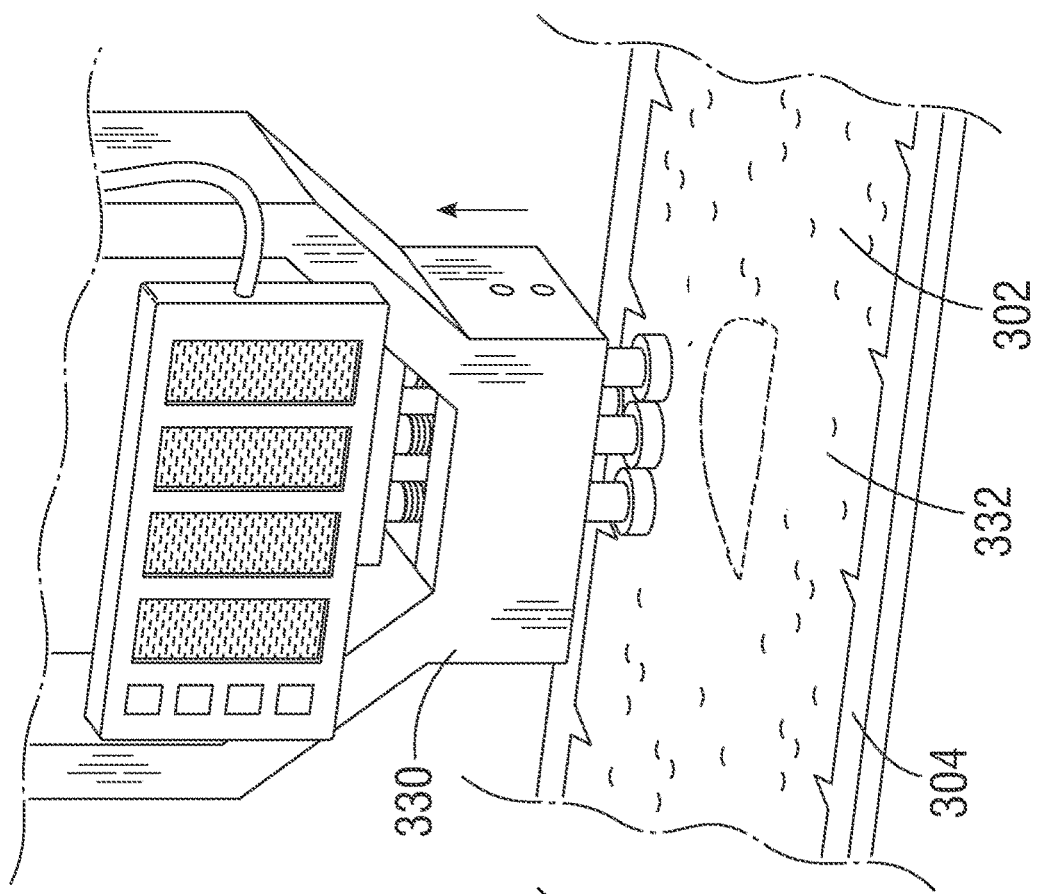
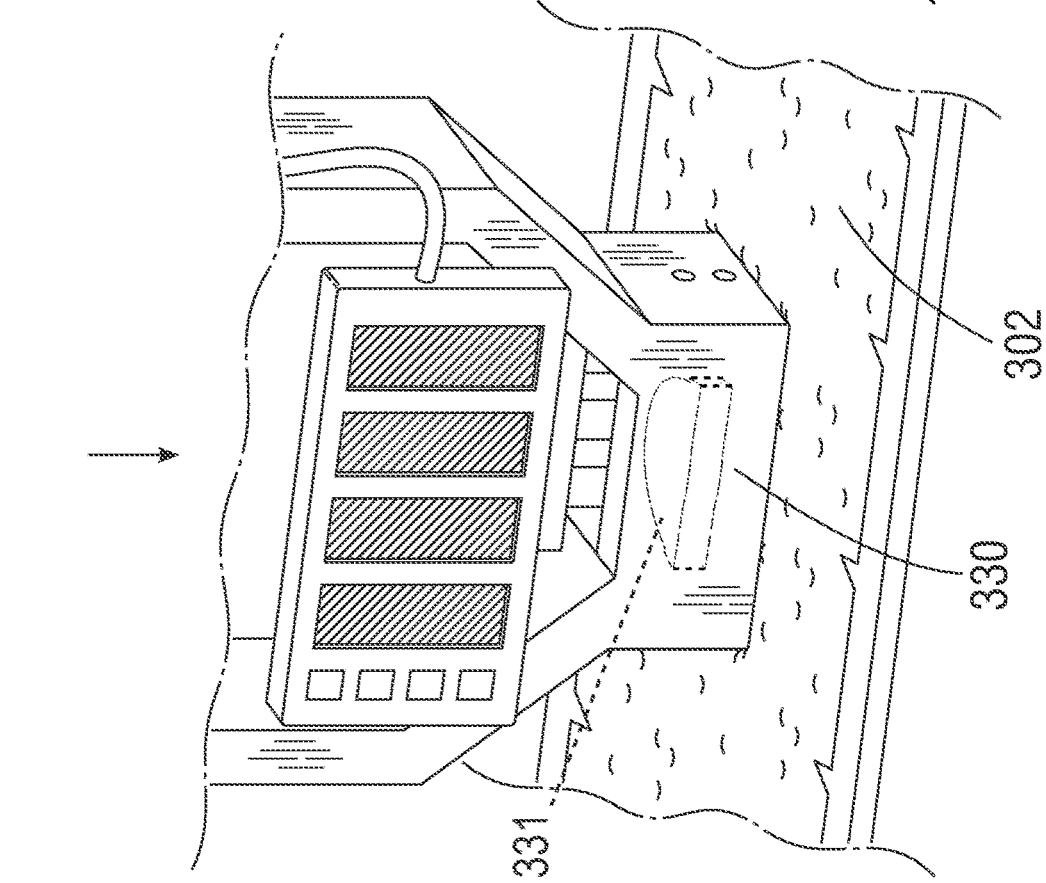

SYSTEMS FOR ASSESSING AND CUTTING BIOPROSTHETIC TISSUE

CROSS REFERENCE TO RELATED APPLICATIONS

This application is a divisional of U.S. patent application Ser. No. 16/459,543, filed Jul. 1, 2019, now U.S. Pat. No. 11,076,953, which is a continuation of U.S. patent application Ser. No. 15/173,435, filed Jun. 3, 2016, now U.S. Pat. No. 10,335,271, which is a divisional of U.S. patent application Ser. No. 13/538,684, filed Jun. 29, 2012, now U.S. Pat. No. 9,358,107, which claims the benefit of U.S. Patent Application No. 61/503,471, filed Jun. 30, 2011, the entire contents all of which are incorporated herein by reference for all purposes.

FIELD OF THE INVENTION

The inventive subject matter generally relates to processing pericardial tissue, and more particularly relates to systems and methods for assessing and cutting pericardial tissue for the manufacture of prosthetic heart valves.

BACKGROUND OF THE INVENTION

A heart of a mammalian animal is a hollow muscular organ having left and right atria and left and right ventricles, each provided with its own one-way valve. A natural heart includes aortic, mitral (or bicuspid), tricuspid and pulmonary valves, and each valve has one-way leaflets to control a directional flow of blood through the heart. The valves are each supported by an annulus that comprises a dense fibrous ring attached either directly or indirectly to the atrial or ventricular muscle fibers. Over time, the heart (, the valve) may become diseased or damaged. To repair the heart, the valve may undergo a valve replacement operation. In one operation, the damaged leaflets of the valve are excised, and the annulus is sculpted to receive a replacement valve, such as a prosthetic heart valve. Although various types and configurations of prosthetic heart valves for replacing diseased natural human heart valves are known, such valves conventionally comprise a valve and a sewing ring supporting valve leaflets and commissure posts.

Bio-prosthetic valves can be formed from an intact, multi-leaflet porcine (pig) heart valve, or by shaping a plurality of individual leaflets out of bovine (cow) pericardial tissue and combining the leaflets to form the valve. The pericardium is a sac around the heart of vertebrate animals, and bovine pericardium is commonly used to make individual leaflets for prosthetic heart valves.

Steps in a typical commercial process for preparing pericardial tissue for heart valve leaflets include first obtaining a fresh pericardial sac, and then cutting the sac open along predetermined anatomical landmarks. The sac is then flattened and typically cleaned of excess fat and other impurities. After trimming obviously unusable areas, a window or patch of tissue is fixed, typically by immersing in an aldehyde to cross-link the tissue. Rough edges of the tissue window are removed and the tissue bio-sorted to result in a tissue section. The process of bio-sorting involves visually inspecting the window for unusable areas, and trimming the section therefrom.

The section is then placed flat on a platform for thickness measurement using a contact indicator. The thickness is measured by moving the section around the platform while a spindle of the indicator moves up-and-down at various points. The thickness at each point is displayed and recorded. After sorting the measured sections by thickness, leaflets are die cut from the sections, with thinner leaflets generally being used for smaller valves, and thicker leaflets being used for larger valves. Of course, this process is relatively time-consuming and the quality of the final leaflets is dependent at several steps on the skill of the technician. Moreover, the number of leaflets obtained from each sac is inconsistent, and subject to some inefficiency from the manual selection process.

To help speed up the process of identifying areas of similar thickness in the pericardial sections, a system and method to topographically map the sheet into similar thickness zones for later use is disclosed in U.S. Pat. No. 6,378,221 to Ekholm, Jr., et al. The system includes a three-axis programmable controller for manipulating a biomaterial workpiece with respect to a thickness measurement head which has a plurality of thickness gauges or sensors for simultaneous measurement of a plurality of points, with the sensors being adapted to contact the sheet or not. A marking head may be provided for marking the zones or otherwise indicating the thickness in different areas. The measured or marked sheet is then removed from the system for further processing into leaflets.

Despite advancements in assessing bioprosthetic tissue for heart valve leaflets and other uses, there remains a need for a more accurate and efficient process. Additionally, the need is more important for thinner leaflets, such as used in smaller surgical valves or in compressible/expandable valves for percutaneous or minimally-invasive surgeries, since the presence of uneven or mismatched leaflets is relatively more detrimental to proper valve functioning.

SUMMARY OF THE INVENTION

In an embodiment, by way of example only, a method of processing pericardial tissue is provided. The method includes positioning a die-cut assembly over the pericardial tissue, the die-cut assembly including a die having a plate, a die pattern, and an opening, the die pattern attached to the plate, the opening formed in the plate to provide access to the pericardial tissue, measuring a thickness of the tissue through the opening, selecting a section of the pericardial tissue based on the thickness measurement, and cutting the pericardial tissue with the die. The die-cut assembly may be mounted for automated vertical movement, and a platen on which the tissue is placed is capable of automated horizontal movement. Different target areas on the tissue can be assessed by measuring the thickness through the die, and when an area is deemed suitable the die pattern cuts a shape therefrom. The system is useful for cutting uniform thickness heart valve leaflets, and can be automated to speed up the process.

In another embodiment, by way of example only, a die is provided for forming a leaflet of a prosthetic valve. The die includes a plate, a die pattern attached to the plate and having a shape resembling the leaflet and defining a boundary, and an opening formed through the plate within the boundary of the die.

In still another embodiment, by way of example only, a system for processing pericardial tissue is provided. The system includes a die and a shield. The die has a plate, a die pattern, a cutting edge, and an opening. The die pattern is attached to the plate and has a shape defining a boundary. The opening is formed through the plate within the boundary of the die pattern. The shield is configured to be disposed between the die and the pericardial tissue to prevent contact between the cutting edge of the die and the tissue, and the shield has a window configured to receive the die pattern.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

FIGS. 9A-9D illustrate a semi-automated system for assessing and cutting heart valve leaflets from pericardial tissue.

DETAILED DESCRIPTION OF THE PREFERRED EMBODIMENTS

The following detailed description is merely exemplary in nature and is not intended to limit the inventive subject matter or the application and uses of the inventive subject matter. Furthermore, there is no intention to be bound by any theory presented in the preceding background or the following detailed description.

Typically, methods of preparing pericardial tissue for use in the formation of bio-prosthetic valve leaflets involve cutting out patches from the tissue and measuring the thickness or other physical characteristics of the tissue patch, sorting the tissue patches based on these physical characteristics, cutting the tissue into the shape of a leaflet, and then sending the tissue on for further processing. Each step of the process is performed separately.

Improved systems and methods for processing pericardial tissue into heart valve leaflets are provided. Generally, the systems include a thickness gauge, a die and a shield. The die has a plate, a die pattern, a sharp cutting edge, and an opening. The die pattern is attached to the plate and has a shape defining a boundary. The opening is formed through the plate within the boundary of the die pattern. The shield is configured to be disposed between the die and the pericardial tissue to prevent inadvertent damage to the tissue from the sharp cutting edge of the die and has a window configured to receive the die pattern. The systems and methods can be used in the manufacture of valve leaflets or other components of a bio-prosthetic heart valve. For example, other prosthetic valve components typically having thickness specifications may benefit from the improved systems and methods as well. These systems and methods allow for the optimization of the valve leaflet formation process.

Figure 1:
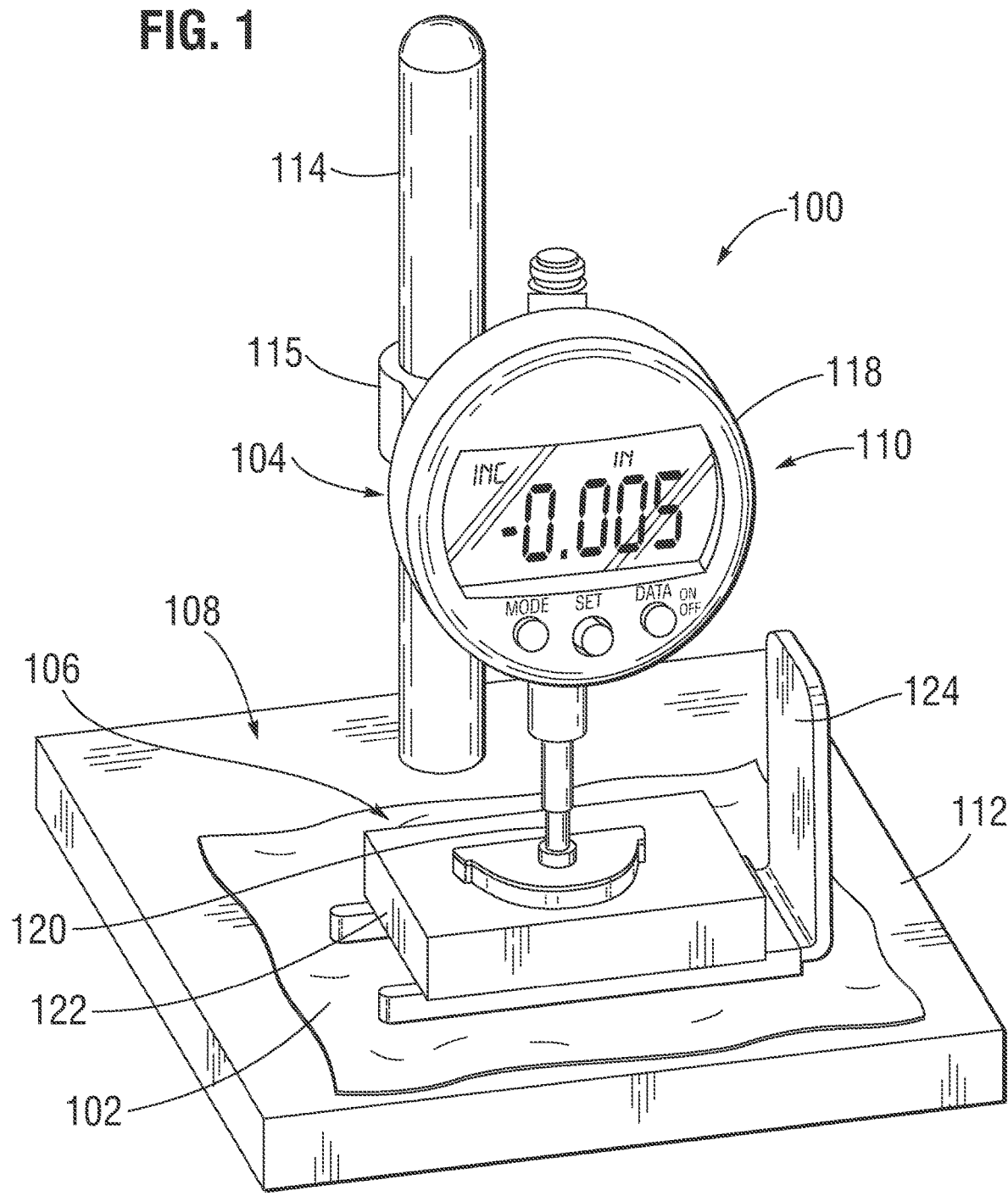
FIG. 1 is a perspective view of a system for assessing and cutting pericardial tissues, according to an embodiment.

FIG. 1 is a perspective view of a system 100 for processing pericardial tissue 102, according to an embodiment. The system 100 includes a thickness gauge 104 and a die-cut assembly 106. The thickness gauge 104 is configured to measure a thickness of the tissue 102 and includes a stand 108 and a detection component 110. The stand 108 has a platform 112 that is sized and shaped to provide a surface on which the tissue 102 can be positioned. In an embodiment, the platform 112 is generally rectangular. In other embodiments, the platform 112 is round, oval or has another configuration. The stand 108 can also include a mounting rod 114 that is coupled to the platform 112. For example, the mounting rod 114 extends generally perpendicular from the platform.

The detection component 110 is mounted to the rod 114 via a coupling arm 115. In an embodiment, the coupling arm 115 has an end through which the mounting rod 114 is inserted and a tightening mechanism for temporary attachment to the rod 114. In this way, the coupling arm 115 can be adjusted between various positions along a length of the mounting rod 114. The detection component 110 has a readout component 118 that is attached to an opposite end of the coupling arm 115 and is positioned over the tissue 102. In an embodiment, a measurement probe 120 extends directly from the readout component 118 for placement over the tissue 102 to measure the thickness of the tissue.

In other embodiments, the thickness gauge 104 may be a standalone device that does not include stand 108. In such case, the readout component of the thickness gauge can be placed in the vicinity of the tissue 102, and the measurement probe of the readout component, which can extend from a wire or can be wirelessly coupled to the readout component, can be manually positioned over the tissue 102.

The die-cut assembly 106 is placed over the tissue 102 and includes a die 122 and a shield 124. Generally, the shield 124 is used to prevent the sharp, cutting edge of the die from inadvertently contacting the tissue and damaging it. The shield 124 is positioned over a selected spot on the tissue 102, and the die 122 is disposed on the shield 124. The die-cut assembly 106 can be moved from spot to spot on the tissue 102 without damaging the tissue so that areas with undesired thicknesses or blemishes on the tissue 102 can be avoided.

Figure 2:
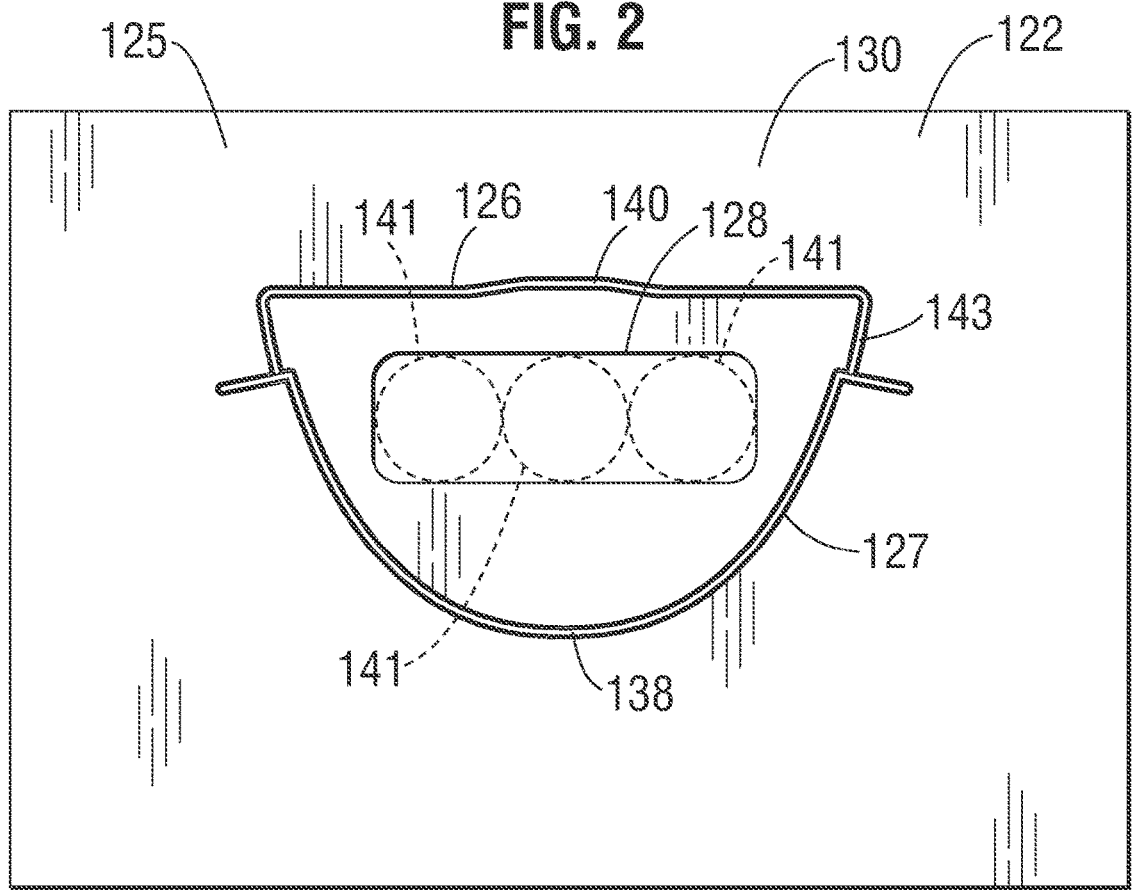
FIG. 2 is a top view of a die assembly for use with the system of FIG. 1, according to an embodiment.
Figure 3:
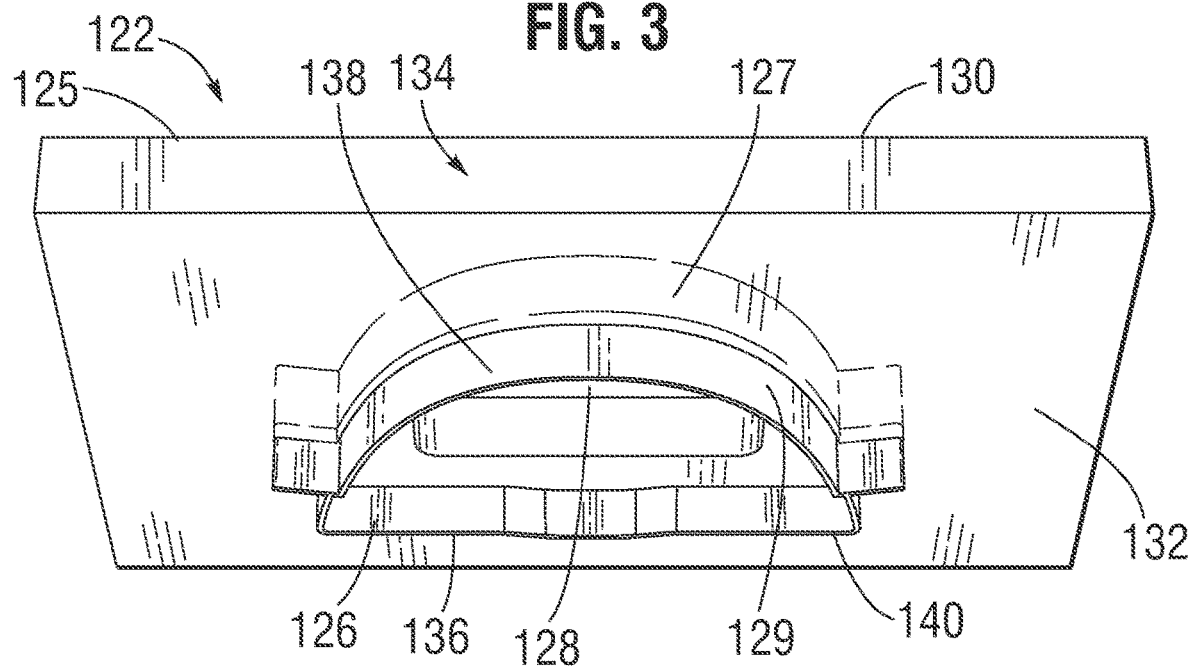
FIG. 3 is a bottom, perspective view of the die assembly of FIG. 2, according to an embodiment.

FIG. 2 is a top view of the die 122 of FIG. 1, and FIG. 3 is a bottom, perspective view of the die assembly of FIG. 2, according to an embodiment. The die 122 is used for identifying a suitable area on the tissue 102 to cut and for then cutting a desired design from the identified area. The die 122 includes a plate 125, a die pattern 126, and an opening 128, in an embodiment. The plate 125 provides an area for grasping and can be generally rectangular, in an embodiment. In other embodiments, the plate is round, oval or another shape. The plate 125 includes a first major surface 130, an opposite second major surface 132, and side surfaces 134 extending between the first and second major surfaces 130, 132. To provide sufficient structural integrity, the plate 125 preferably comprises a thermoplastic material including one of an acrylic glass and polycarbonate (PC) material or another shatter-resistant material.

The die pattern 126 is attached to and extends from the first major surface 130. In an example, the die pattern 126 includes a portion 127 that is embedded within the plate 125 and an exposed portion 129 that extends from the plate 125. The exposed portion 129 of the die pattern 126 has a height that is greater than a thickness of the tissue 102. To ensure that the die pattern 126 can pierce through the tissue, the die pattern 126 has a sharpened cutting edge 136 and preferably comprises a metal material. Suitable materials include, but are not limited to, stainless steel and the like.

The die pattern 126 forms a generally closed shape defining a boundary. In an embodiment, the die pattern 126 has a leaflet shape for forming one leaflet used in the manufacture of the bio-prosthetic heart valve. A bio-prosthetic heart valve leaflet typically includes a straight free or coapting edge having opposed tab ends, and a generally semicircular cusp therebetween and opposite the coapting edge. Thus, as illustrated, an exemplary die pattern 126 for cutting a valve leaflet has a curved portion 138 and a straight portion 140 with tab ends 143. In an embodiment, the curved portion 138 is a semicircle. In still another embodiment, the curved portion 138 forms an arc with multiple radii. In an embodiment, the straight portion 140 encloses the curved portion 138 and extends from one end of the curved portion 138 to another. Alternatively, the straight portion 140 includes tabs 143 that extend from the straight portion 140 and couple the straight portion 140 to the curved portion 138. In accordance with another embodiment, the die pattern 126 has a shape for forming another component of the prosthetic heart valve.

The opening 128 is formed through the plate 125 and extends between the first and second major surfaces 130, 132. To insure that the portion of the tissue 102 being measured will have a suitable thickness for formation of the prosthetic valve, the opening 128 is disposed within the boundary of the die pattern 126. In an embodiment, a single opening 128 is formed in the plate 125. In an embodiment, the location of the openings may be adjacent to the straight portion 140 of the die pattern 126. The opening 128 can be rectangular and is dimensioned to accommodate the measurement probe 120 (FIG. 1) of the thickness gauge 104. In another embodiment, the dimensions of the opening 128 are such that at least three thickness measurements can be taken at different spots on the tissue 102.

In another embodiment, more than one opening is included. For example, three openings 141 (shown in phantom in FIG. 2) can be formed in selected locations in the boundary of the die pattern 126. Thus, thickness measurements can be taken in the same place each time and therefore be consistent for each valve component formed using the die 122. The openings 141 are configured to receive the measurement probe 120 (FIG. 1) of the thickness gauge 104. Although the openings 141 are shown as being generally circular, they can have any alternate shape that can accommodate the measurement probe 120.

Figure 4:
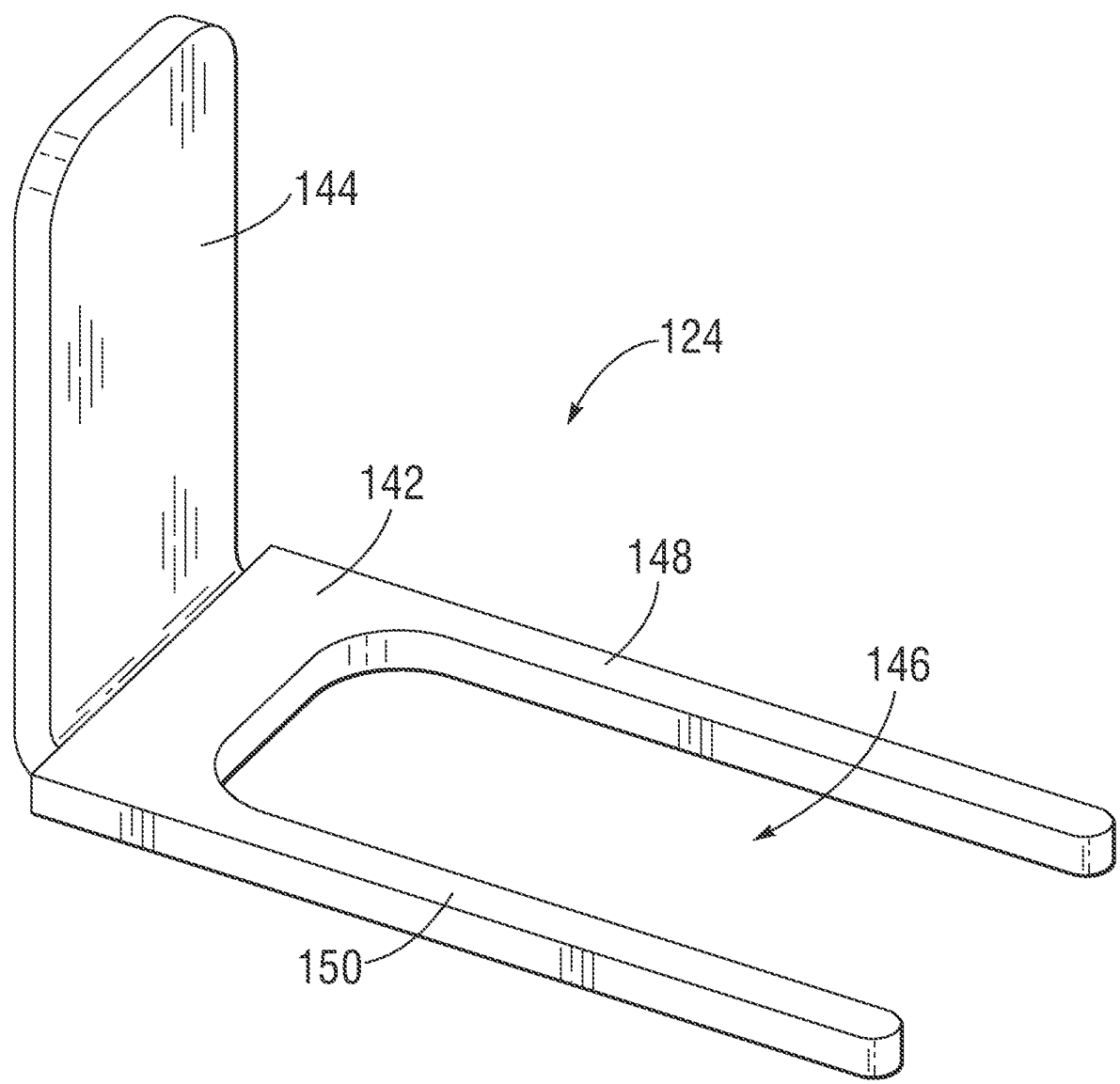
FIG. 4 is a perspective view of a shield for use system of FIG. 2, according to an embodiment.

Turning now to FIG. 4, a perspective view of the shield 124 for use with the system 100 of FIG. 2 is provided, according to an embodiment. The shield 124 preferably comprises a metal material, and in some embodiments, the shield 124 can comprise stainless steel and the like. The shield 124 has a base 142 and a handle 144, in an embodiment. The base 142 has a window 146 that is configured to allow the exposed portion 129 (FIG. 3) of the die pattern 126 to extend. In an embodiment, the base 142 includes two bifurcated prongs 148, 150 that are spaced apart to define a portion of the window 146. In another embodiment, the base 142 has a more solid platen configuration, and the window 146 is formed into the platen configuration. To provide a clearance between the sharpened edge 136 of the die 122 and the tissue 102 to thereby prevent damage to the tissue 102, the base 142 has a thickness that is greater than the height of the exposed portion 129 (FIG. 3) of the die pattern 126.

The handle 144 extends from the base 142 and is configured to provide a grip. Although the handle 144 is illustrated as being substantially rectangular in configuration, other shapes may alternatively be employed. Additionally, although the handle 144 is illustrated as extending substantially perpendicular relative to the base 142 in FIG. 4, it will be appreciated that the handle 144 can extend at another angle relative to the base 142. For example, the handle 144 can be disposed on the same plane as the base 142 and may not be angled relative to the base 142. In another example, the handle 144 is disposed at a 45 degree angle relative to the base 142. In other embodiments, other placement angles may be more conducive.

The shield 124 thus elevates the sharpened edge 136 of the die 122 above the tissue 102 on the platform 112. The bifurcated prongs 148 are useful for supporting the plate 125 to the outside of the exposed portion 129 of the die pattern 126, which avoids blocking the opening 128 or openings. Further, the thin prongs 148 reside outside of the die pattern 126, and thus outside of the subsequently cut leaflet, thus preventing damage to the leaflet by the weight of the prongs. Of course, other arrangements for elevating the sharpened edge 136 above the tissue 102 are contemplated, including mounting the die 122 on a mechanism capable of vertical movement such that the die can be independently elevated and then lowered to cut the leaflet. One such mechanism is described below.

Figure 5:
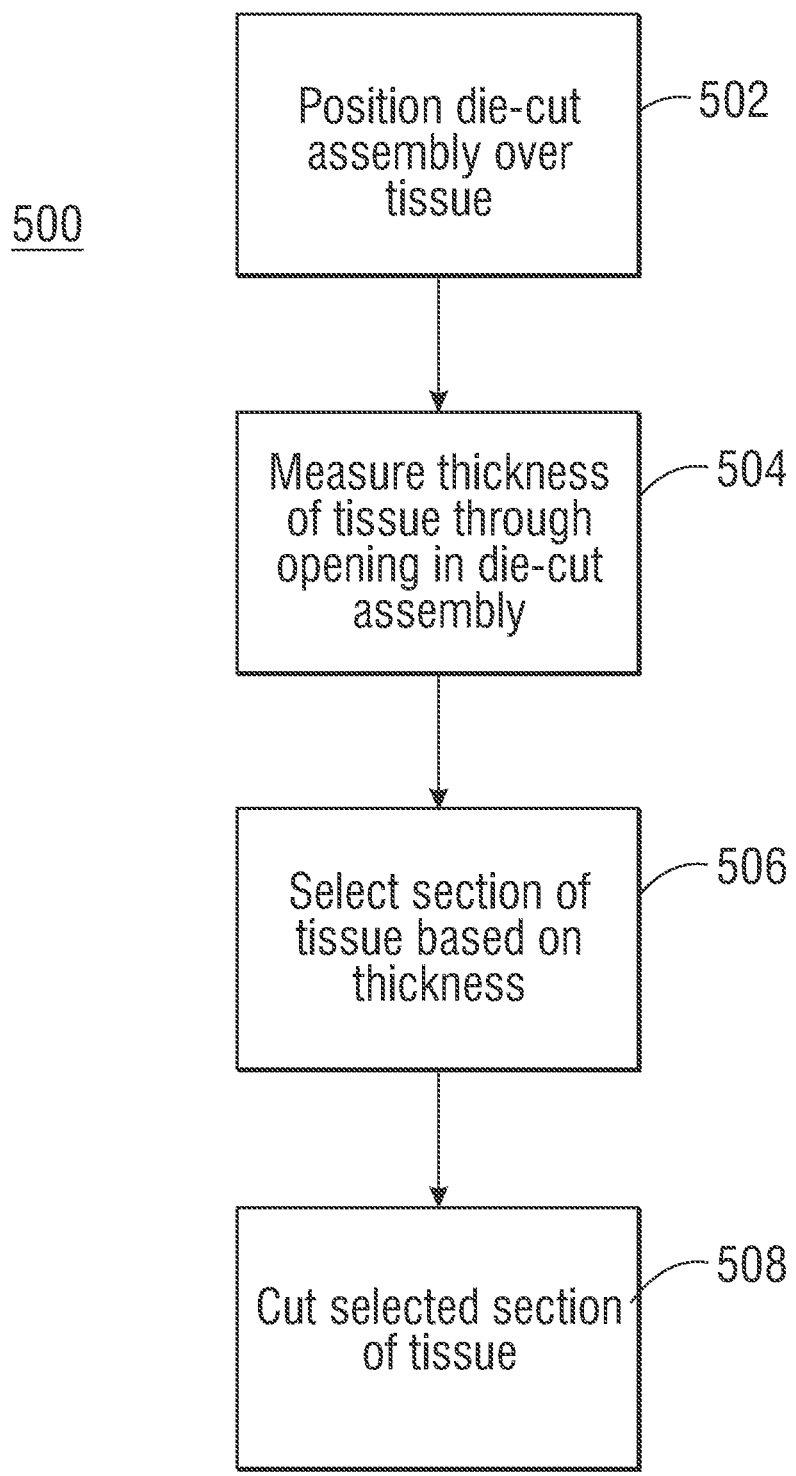
FIG. 5 is a flow diagram of a method of processing pericardial tissue.

FIG. 5 is a flow diagram of a method 500 of processing pericardial tissue. The method 500 includes positioning a die-cut assembly that includes a shield and a thickness gauge over the pericardial tissue, block 502. The die-cut assembly can be configured similar to die-cut assembly 106 of FIG. 1 and includes a die having a plate, a die pattern, and an opening. The die pattern is attached to the plate, and the opening is formed in the plate to provide access to the pericardial tissue which is positioned to lie flat on surface below the die-cut assembly. Next, a thickness of the tissue is measured through the opening, block 504. Thickness is measured by a thickness gauge, such as thickness gauge 104 of FIG. 1. The thickness gauge can include a measurement probe that can perform a single measurement at a time, in an embodiment. In another embodiment, the thickness gauge may have a measurement probe that obtains multiple measurements at several locations simultaneously. Or as described below, a plurality of measurement probes can perform the measurements simultaneously or sequentially.

In an embodiment, the plate includes more than one opening, for example, three openings, and block 504 is performed by measuring the thickness of the tissue through the three openings. As alluded to briefly, in another embodiment, the measurements through the three openings can be performed substantially concurrently by employing a suitably configured thickness gauge. As described in detail above, the shield prevents damage to the tissue from the sharp cutting edge of the die during the measurement of the tissue thickness by elevating the cutting edge above the tissue until it is time to cut the leaflet. At block 506, a section of the pericardial tissue from which a leaflet will be formed is selected, based in part on the thickness measurement of the tissue. Then, the shield is removed and the selected section of the pericardial tissue is cut with the die, block 508, to form the leaflet. The leaflet is then sent on for further processing.

By providing the above-described system 100 and method 500, manufacturing prosthetic valve components, such as leaflets, is both simplified and optimized. Additionally, measuring the thickness of a selected portion of the tissue immediately prior to cutting, and without the need to position or reposition the die prior to cutting, reduces a likelihood of misidentification of an area of the tissue to be cut.

Moreover, by using the aforementioned techniques, formation of the prosthetic valve components is less laborious and less time-consuming.

Figure 6:
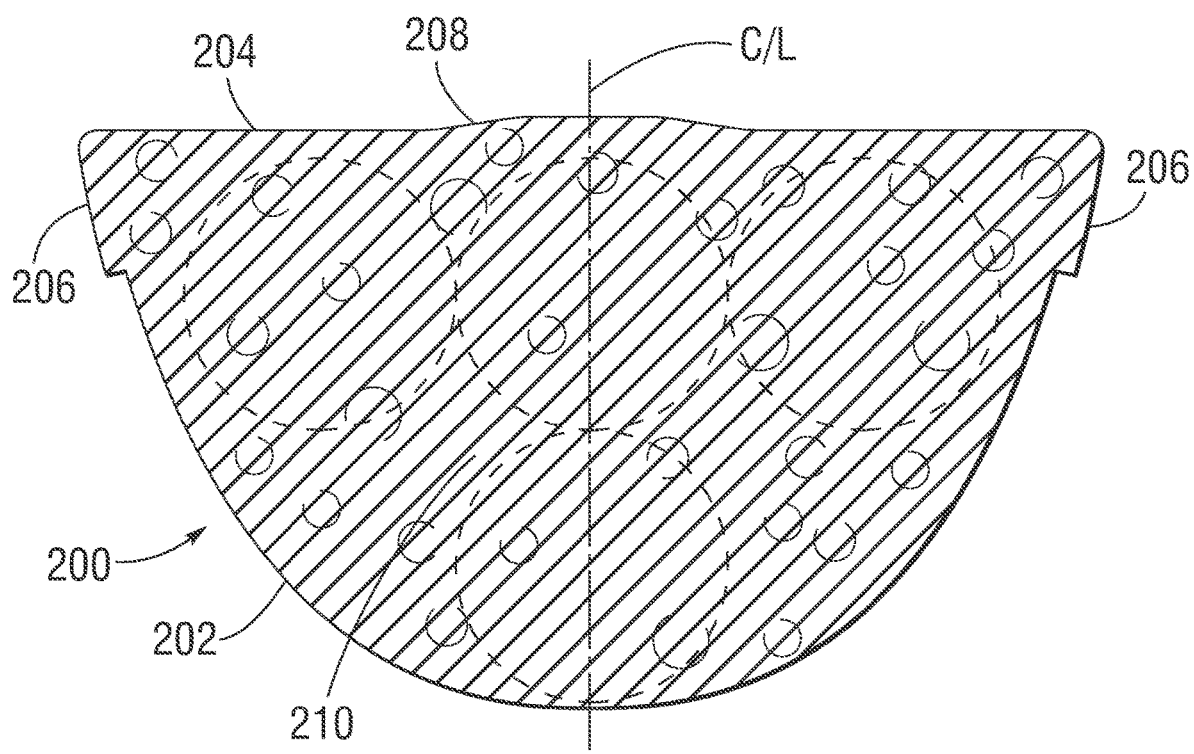
FIG. 6 is a plan view of an exemplary heart valve leaflet cut with a die in accordance with the principles described herein.

FIG. 6 illustrates an exemplary prosthetic heart valve leaflet 200 formed in accordance with the principles of the present application. As mentioned above, the leaflet 200 typically includes an arcuate cusp edge 202 opposite a free or coapting edge 204. A pair of side tabs 206 extends in opposite directions on either side of the coapting edge 204, and in between the coapting edge and the cusp edge 202. The coapting edge 204 may be straight, or may be shaped such as shown to have a slight trapezoidal extension 208 in the middle to facilitate coaptation with the other leaflets. The peripheral edges, including the cusp edge 202, coapting edge 204, and side tabs 206, circumscribe a central region 210. The leaflet 200 is desirably symmetric about a vertical center line C/L. When assembled in a heart valve, three identical leaflets 200 attach along their cusp edges 202 to a surrounding stent structure, with each side tab 206 being attached to the stent structure and to a side tab of an adjacent leaflet. The three coapting edges 202 meet or coapt in the flowstream of the implanted valve to close off backflow in diastole, and are then forced open in systole. The stresses on the leaflets from the oscillating fluid flow are greatest toward the edges where the leaflets attach (typically with sutures) to the stent structure (or fabric coverings thereof). Indeed, the tabs 206 are preferably wrapped around a portion of the stent structure and secured thereto for added strength.

The desired thickness of bovine pericardium for heart valve leaflets varies with the size of the leaflets, with smaller leaflets generally being thinner than larger leaflets. Preferably, a majority of each leaflet is a single desired thickness. Typically, harvested bovine pericardial tissue ranges in thickness from 250 microns up to 700 microns, though most of the material is between 300-700 microns thick. Heart valves with extended durability have had bovine pericardial leaflet thicknesses ranging from 0.009-0.023 inches (~230-580 microns), with smaller valves utilizing thinner leaflets and larger valves having thicker leaflets.

Figure 7:
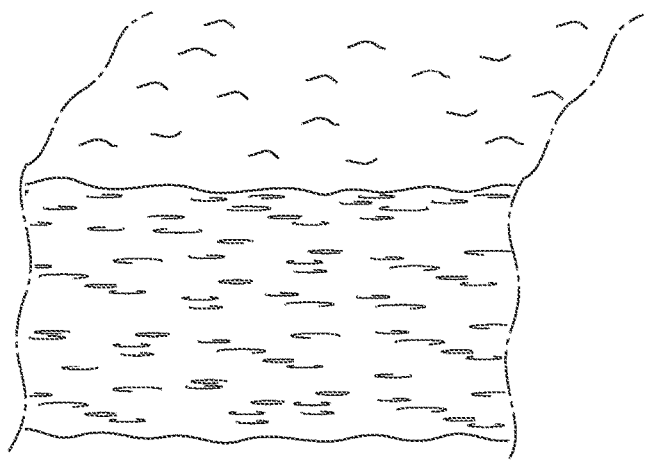
FIGS. 7 and 8 are magnified sectional views through exemplary bioprosthetic tissue illustrating typical physical compositions.
Figure 8:
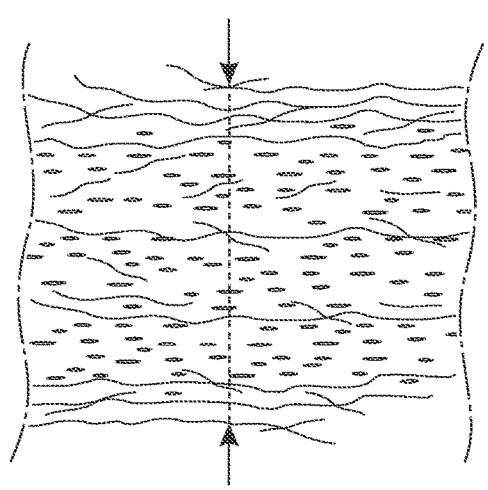

FIGS. 7 and 8 are magnified perspective and sectional views of two samples of fixed bovine pericardial tissue. These views illustrate the somewhat uneven cross-sectional composition of the tissue, as well as a porous or generally heterogenous structure, in particular as seen in FIG. 8. The present application accommodates the varied physical structure of bioprosthetic tissue, in particular bovine pericardium. That is, the measurements are done using a thickness gauge having a contact probe which lightly compresses the tissue for a predetermined time period. FIG. 7 shows a sample of fixed bovine pericardium having a generally uniform thickness, which would be suitable for use in forming leaflets for a bioprosthetic heart valve.

FIGS. 9A-9D illustrate a semi-automated system 300 for assessing and cutting heart valve leaflets from pericardial tissue 302. The tissue 302 is shown as an enlarged sheet which can be formed from a pericardial sac, using bovine, equine, porcine, or other such animal sources. The tissue 302 lies flat on a platen 304 that is desirably movable in two or three axes underneath a measurement and cutting head 310. An outline of a heart valve leaflet 306 is shown beneath the measurement and cutting head 310, along with the outline of four circles 308 within the leaflet outline. The outlines of the leaflet 306 and circles 308 are shown merely to illustrate the location of a target area being assessed underneath the head 310.

The measurement and cutting head 310 includes a plurality of vertical distance thickness gauges or measurement sensors that end in contact probes 312 arranged in a particular pattern over the target area of the leaflet outline 306. More specifically, the vertical profile of the sensor probes 312 is indicated by the circles 308 within the leaflet outline. That is, when the sensor probes 312 descend to measure the thickness of the tissue 302, they contact the tissue at the circles 308. In the illustrated embodiment, there are four such sensor probes 312 arranged substantially contiguously within the leaflet outline 306.

A preferred arrangement of sensor probes 312 is shown in phantom in the plan view of the leaflet 200 of FIG. 6. In particular, three sensor probes 312 contact the tissue substantially in a line, while a fourth sensor 312 contacts the tissue at a location that is perpendicular to the middle of the three sensors. This abbreviated T-shaped pattern is intended to provide a thickness measurement for a heart valve leaflet that substantially encompasses the central region 210, within the peripheral edges 202, 204, 206. The four sensors 312 thus provide a relatively accurate measurement of an area of tissue large enough from which to cut a heart valve leaflet.

In any event, the number of sensor probes 312 and their pattern can vary. For example, for an even more accurate measurement of thickness, more than four sensors can be utilized to obtain more data points. Alternatively, a single sensor can be used which is moved to the four locations shown, though the process takes a bit longer. Furthermore, the relative locations of the sensors can be modified to provide measurements of particular patterns across an area to be cut into a leaflet. For example, measurements of the thickness along radial lines from the center of the coapting edge 204 to the arcuate cusp edge 202 can be made to obtain leaflets having uniform thicknesses along these radial lines. Likewise, measurements of the area corresponding to the cusp edge 202 can be made to ensure that the tissue in the area is no thinner than the central region 210.

The sensor probes 312 are desirably stainless steel with circular feet. The feet are dropped from a small height so as to lightly compress the tissue for a predetermined time period and obtain a measurement of the physical thickness by compressing any unduly porous portions of the tissue. All four probes can be dropped at once, or they can be actuated sequentially. Preferably, the compressive force exerted on the tissue by each probe is the same as the other probes, and a force sensor may be included in the platen 304, for example, to ensure uniformity. Alternatively, periodic monitoring may be done, such as measuring the probe drop force before and/or after a series of thickness measurements are taken.

With reference back to FIG. 9A, the measurement and cutting head 310 further includes an indicator display 320 and a plurality of LED panels 324 along the front, the number of which corresponds to the number of sensors 312. An electronic control and feedback system (not shown) is calibrated to change the color of the LED panels 324 based on the measurements taken by the four sensors 312. More particularly, the color of the respective LED panel 324 desirably changes from off (gray) to green when the thickness measured by each of the sensors 312 falls within a particular range. For instance, for a small bovine pericardial leaflet desirably having a thickness of between 0.009-0.011 inches (~230-280 microns), each of the LED panels 324 is illuminated with green LEDs if the respective sensor 312 measures between that thickness range. Alternatively, an actual thickness readout may be provided for each sensor 312, as well as other equivalent indicators.

The measurements and cutting head 310 further includes a cutting assembly 330 including a cutting die (schematically shown at 331 in FIG. 9C) in the shape of a heart valve leaflet mounted to the underside thereof. The cutting die may be similar to the die described above for use in a more manual operation, and typically includes a die pattern having a lower sharpened edge. The cutting assembly 330 thus corresponds to the die 122 described above, and includes openings through which the measurement sensor probes 312 pass.

In the sequence of FIGS. 9A-9D, the operator (or computer, if machine controlled) locates a predetermined untested patch of tissue 302 beneath the measurement and cutting head 310. For instance, in FIG. 9A the dashed outline of the leaflet 306 indicates the area to be tested. The four LED panels 324 are showing gray, or off, to indicate no measurement has been taken. Then, as in FIG. 9B, the sensor probes 312 are dropped onto the tissue 302, either simultaneously or one-by-one. The outputs of each of the sensor 312 readings shows up on the LED panels 324 as either a green color for a measurement within the desired range, or a red color to indicate outside the range. As can be seen, all four LED panels 324 are green, signifying that the area of tissue underneath the measurement and cutting head 310 is suitable for that particular thickness of leaflet. FIG. 9C shows the cutting assembly 330 lowered so that the leaflet cutting die (schematically shown at 331) contacts the tissue 302 and cuts the leaflet. Just prior to or during this stage the sensor probes are lifted back to their original raised positions. Finally, FIG. 9D shows the cutting assembly 330 having been raised, revealing a cut leaflet 332. The leaflet can be removed for further processing, or more areas of the tissue 302 may be assessed and more leaflets cut, if appropriate. It will be apparent to those of skill in the art that setting up a bovine pericardial sac on the platen 304 and programming a control system enables the entire sac to be assessed and leaflets cut therefrom without further operator input.

The measurement sensors may take a variety of forms, but can generally be categorized as those sensors that contact the bio-material. Contact sensors are designed to produce a signal upon contact with the bio-material that, in combination with knowledge of the relative height of the sensor above the work surface, determines the thickness of the bio-material. The present invention encompasses any sensor that can detect the thickness of a material relative to a reference surface on which the material is placed.

While embodiments and applications of this invention have been shown and described, it would be apparent to those skilled in the art that many more modifications are possible without departing from the inventive concepts herein, and it is to be understood that the words which have been used are words of description and not of limitation. Therefore, changes may be made within the appended claims without departing from the true scope of the invention.

What is claimed is:

1. A system for assessing and cutting sheet bioprosthetic tissue, comprising:
    a flat platen on which a sheet of bioprosthetic tissue may be supported;
    a measurement and cutting head mounted above the platen having a vertically-movable die for cutting bioprosthetic tissue on the platen, the die having a sharp die cutting pattern defining an opening within an outer boundary, the measurement and cutting head comprising an automated elevation system that can raise or lower the die to various heights relative to the platen and a distance measurement gauge with a vertically movable probe adapted to pass through the opening and measure the thickness of the bioprosthetic tissue on the platen;
    an indicator panel that displays the indication of tissue thickness from the probe; and
    a die control for lowering the die and cut bioprosthetic tissue on the platen.

2. The system of claim 1, wherein the die includes a plate defining a plurality of the openings within the outer boundary.

3. The system of claim 2, wherein the distance measurement gauge has a plurality of the vertically movable probes each of which is aligned with one of the openings, and the indicator panel displays the indication of tissue thickness from all of the probes.

4. The system of claim 1, wherein the distance measurement gauge has a plurality of the vertically movable probes which are aligned to pass simultaneously through the opening within the outer boundary, and the indicator panel displays the indication of tissue thickness from all of the probes.

5. The system of claim 4, wherein the indicator panel has a plurality of LED indicators, one for each probe, and the indicator panel is calibrated to illuminate each LED with a particular color when the associated probe measures the tissue thickness within a predetermined desirable range.

6. The system of claim 1, wherein the vertically movable probe is weighted and configured to be dropped from a predetermined height so as to compress the bioprosthetic tissue, and the distance measurement gauge is calibrated to leave the probe in a dropped position for a predetermined time period prior to measuring the thickness of the tissue with the probe.

7. The system of claim 6, wherein the vertically movable probe is stainless steel with a circular foot that contacts the bioprosthetic tissue.

8. The system of claim 1, further including an automated movement system adapted to displace the platen horizontally in two axes under the measurement and cutting head.

9. The system of claim 8, wherein the automated movement system is adapted to displace the platen in three axes.

10. The system of claim 1, wherein the die cutting pattern is in the shape of a heart valve leaflet, and there are at least three of the vertically movable probes.

11. A system for assessing and cutting sheet bioprosthetic tissue, comprising:
    a flat platen on which a sheet of bioprosthetic tissue may be supported;
    a measurement and cutting head mounted above the platen having a vertically-movable die for cutting bioprosthetic tissue on the platen, the die having a sharp die cutting pattern defining an opening within an outer boundary, the measurement and cutting head comprising a plurality of vertically movable probes each adapted to pass through the opening and measure the thickness of the bioprosthetic tissue on the platen;
    an indicator panel that displays the indication of tissue thickness from the probes, wherein the indicator panel is calibrated to provide a positive indication when each probe measures the tissue thickness within a predetermined desirable range; and
    a die control for lowering the die and cut bioprosthetic tissue on the platen.

12. The system of claim 11, wherein the die includes a plate defining a plurality of the openings within the outer boundary.

13. The system of claim 12, wherein the each of the vertically movable probes is aligned with one of the openings.

14. The system of claim 11, wherein the opening is large enough for all of the vertically movable probes to pass simultaneously therethrough.

15. The system of claim 11, wherein the indicator panel has a plurality of LED indicators, one for each probe, and the indicator panel is calibrated to illuminate each LED with a particular color when the associated probe measures the tissue thickness within the predetermined desirable range.

16. The system of claim 11, wherein the vertically movable probes are weighted and configured to be dropped from a predetermined height so as to compress the bioprosthetic tissue, and the distance measurement gauge is calibrated to leave the probe in a dropped position for a predetermined time period prior to measuring the thickness of the tissue with the probe.

17. The system of claim 16, wherein the vertically movable probe is stainless steel with a circular foot that contacts the bioprosthetic tissue.

18. The system of claim 11, further including an automated movement system adapted to displace the platen horizontally in two axes under the measurement and cutting head.

19. The system of claim 18, wherein the automated movement system is adapted to displace the platen in three axes.

20. The system of claim 18, wherein the measurement and cutting head comprises an automated elevation system that can raise or lower the die to various heights relative to the platen.

21. The system of claim 11, wherein the die cutting pattern is in the shape of a heart valve leaflet, and there are at least three of the vertically movable probes.

* * * * *